(12) United States Patent
Murad

(10) Patent No.: US 8,051,946 B1
(45) Date of Patent: Nov. 8, 2011

(54) STETHOSCOPE SHIELD DEVICE

(76) Inventor: Elias Murad, Fontana, CA (US)

(*) Notice: Subject to any disclaimer, the term of this patent is extended or adjusted under 35 U.S.C. 154(b) by 0 days.

(21) Appl. No.: 12/804,933

(22) Filed: Aug. 2, 2010

Related U.S. Application Data

(60) Provisional application No. 61/281,602, filed on Nov. 19, 2009.

(51) Int. Cl.
*A61B 7/02* (2006.01)
(52) U.S. Cl. .................................................. 181/131
(58) Field of Classification Search ............ 181/131
See application file for complete search history.

(56) References Cited

U.S. PATENT DOCUMENTS

| | | | | |
|---|---|---|---|---|
| 5,365,023 A * | 11/1994 | Lawton | ........................ | 181/131 |
| 5,424,495 A * | 6/1995 | Wurzburger | .................. | 181/131 |
| 5,428,193 A | 6/1995 | Mandiberg | | |
| 5,528,004 A * | 6/1996 | Wurzburger | .................. | 181/131 |
| 5,686,706 A * | 11/1997 | Wurzburger | .................. | 181/131 |
| 6,009,971 A * | 1/2000 | Weidman et al. | ............. | 181/131 |
| 6,019,187 A | 2/2000 | Appavu | | |
| 6,206,134 B1 | 3/2001 | Stark et al. | | |
| 2005/0257996 A1* | 11/2005 | Brown et al. | .................. | 181/131 |
| 2007/0045039 A1* | 3/2007 | Agahi et al. | .................. | 181/131 |

* cited by examiner

*Primary Examiner* — Forrest M Phillips
(74) *Attorney, Agent, or Firm* — Emery L. Tracy

(57) ABSTRACT

A stethoscope shield device for protecting a chestpiece of a stethoscope is provided. The chestpiece has a diaphragm side and a bell side. The stethoscope shield device comprises a support member for covering at least a portion of one of the sides of the chestpiece with the support member having a perimeter edge and constructed for retaining and maintaining a desired shape. A securing body is secured to the perimeter of the support member with the securing body having an aperture positionable about the chestpiece between the diaphragm side and the bell side. An elastic band encircles the aperture formed in the securing body wherein the elastic band releasably secures the stethoscope shield device to the stethoscope and maintains a snug, tight fit around the chestpiece of the stethoscope.

19 Claims, 1 Drawing Sheet

025
STETHOSCOPE SHIELD DEVICE

The present application claims the benefit of priority of pending provisional patent application Ser. No. 61/281,602, filed on Nov. 19, 2009, entitled "Stethoscope Shield".

BACKGROUND OF THE INVENTION

1. Field of the Invention

This invention relates generally to a stethoscope shield device and, more particularly, the invention relates to a stethoscope shield device for alleviating contamination on the heads of stethoscopes.

2. Description of the Prior Art

Perhaps one of the most important diagnostic tools used by those in the heath care industry is the simple stethoscope. Designed to enable the professional to easily listen to sounds emitted by various parts of the patient's body, a stethoscope is used by everyone from doctors and nurses, to paramedics and emergency technicians. The modern stethoscope is designed with much more knowledge about the transmission of sound. Stethoscopes are fitted with two ear pieces and tubing of a special length between patient and doctor. Special heads pick up both high and low pitched sounds. An experienced doctor can listen to all the body's sounds and interpret their meaning. Thanks to the stethoscope, he or she can hear all the body's special messages and use this audio information as a very effective diagnostic tool. As such, a stethoscope is the first item many purchase when completing their medical training and most medical personnel utilize their own stethoscope when treating patients. Not surprisingly, because these devices are utilized repeatedly throughout the day on dozens of patients, it stands to reason that the equipment can possibly become contaminated. A lingering germs or bacteria from one patient could possibly be transferred to the next patient upon which the stethoscope is placed.

SUMMARY

The present invention is a stethoscope shield device for protecting a chestpiece of a stethoscope. The chestpiece has a diaphragm side and a bell side. The stethoscope shield device comprises a support member for covering at least a portion of one of the sides of the chestpiece with the support member having a perimeter edge and constructed for retaining and maintaining a desired shape. A securing body is secured to the perimeter of the support member with the securing body having an aperture positionable about the chestpiece between the diaphragm side and the bell side. An elastic band encircles the aperture formed in the securing body wherein the elastic band releasably secures the stethoscope shield device to the stethoscope and maintains a snug, tight fit around the chestpiece of the stethoscope.

In addition, the present invention includes a method for protecting a chestpiece of a stethoscope. The chestpiece has a diaphragm side and a bell side. The method comprises providing a support member having a perimeter edge, covering at least a portion of one of the sides of the chestpiece with the a support member with the support member having a perimeter edge, retaining and maintaining a desired shape of the support member, providing a securing body having an aperture, securing the securing body to the perimeter of the support member, positioning the aperture about the chestpiece between the diaphragm side and the bell side, encircling the aperture with an elastic band, releasably securing the stethoscope shield device to the stethoscope, and maintaining a snug, tight fit around the chestpiece of the stethoscope.

The present invention further includes a stethoscope shield device for protecting a chestpiece of a stethoscope. The chestpiece has a diaphragm side and a bell side. The stethoscope shield device comprises a support member for covering at least a portion of one of the sides of the chestpiece with the support member having a perimeter edge and constructed for retaining and maintaining a desired shape. A securing body is secured to the perimeter of the support member with the securing body having an aperture positionable about the chestpiece between the diaphragm side and the bell side. An elastic band encircles the aperture formed in the securing body. An attachment/removal mechanism assists in attaching and removing the stethoscope shield device to the chestpiece of the stethoscope. The elastic band releasably secures the stethoscope shield device to the stethoscope and maintains a snug, tight fit around the chestpiece of the stethoscope and the securing body material is thinner and more flexible than the support member material.

DETAILED DESCRIPTION OF THE PREFERRED EMBODIMENTS

Figures 1, 2, 3:
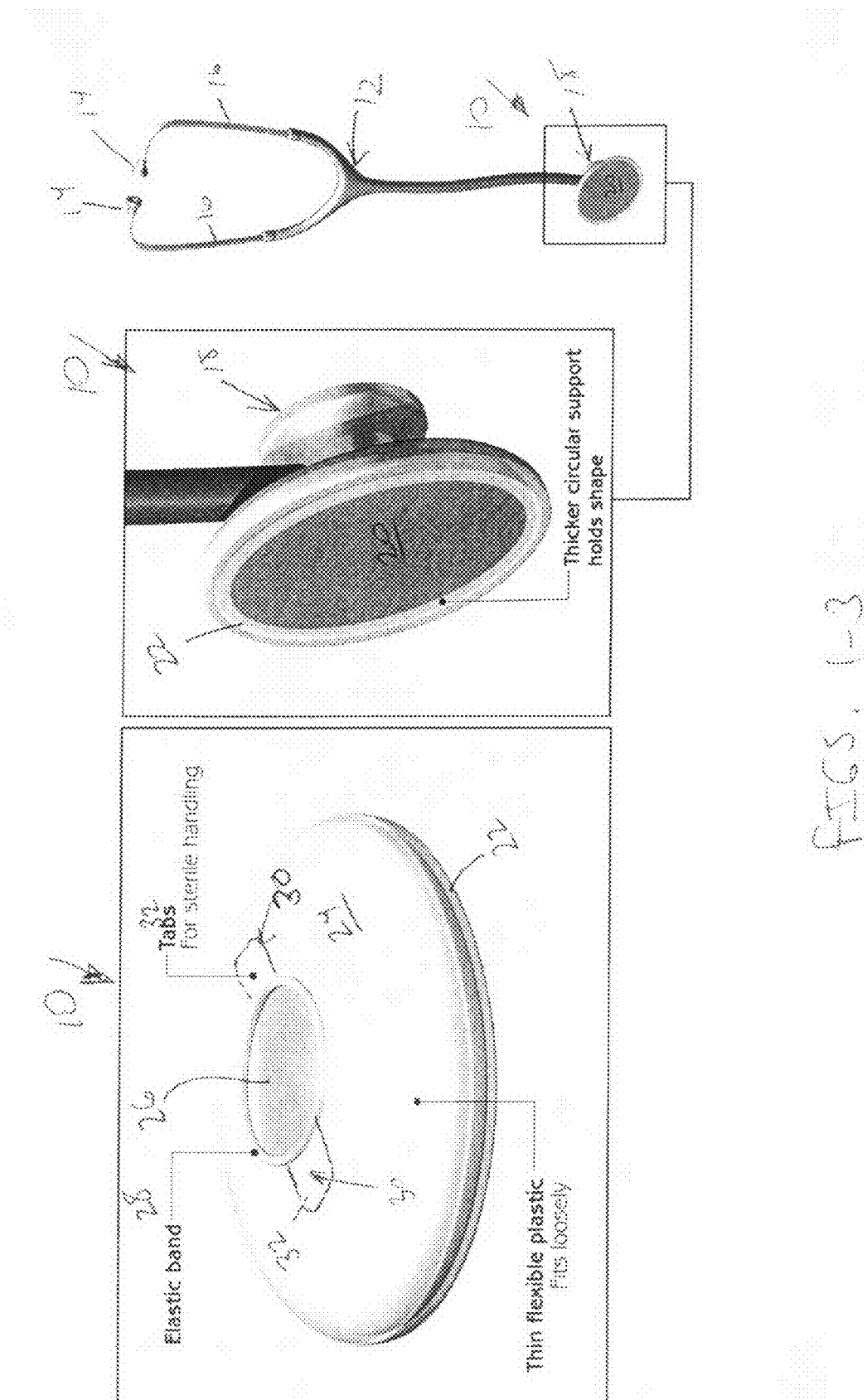
FIG. 1 is a perspective view illustrating a stethoscope shield device, constructed in accordance with the present invention.
FIG. 2 is a perspective view illustrating the stethoscope shield device of FIG. 1, constructed in accordance with the present invention, with the stethoscope shield device releasably secured to a stethoscope.
FIG. 3 is another perspective view illustrating the stethoscope shield device of FIG. 1, constructed in accordance with the present invention, with the stethoscope shield device releasably secured to a stethoscope.

As illustrated in FIGS. 1-3, the present invention is a stethoscope shield device, indicated generally at 10, for protecting a stethoscope 12. A stethoscope 12 typically includes a pair of earpieces 14 connected at one end of a pair of hollow tubing 16. At the opposite end of the tubing 16 is a chestpiece 18 usually consisting of two sides positionable against the patient for sensing sound: a diaphragm (plastic disc) and a bell (hollow cup). If the diaphragm is placed on the patient, body sounds vibrate the diaphragm, creating acoustic pressure waves which travel up the tubing to the listener's ears. If the bell is placed on the patient, the vibrations of the skin directly produce acoustic pressure waves traveling up to the listener's ears. The bell transmits low frequency sounds, while the diaphragm transmits higher frequency sounds.

The stethoscope shield device 10 of the present invention is a specially designed, protective sheath for covering either or both sides of a stethoscope chestpiece 18 for inhibiting contamination of the chestpiece 18. Preferably, the sheath has a circular support member 20 having an outer perimeter 22 with the circular support member 20 extending completely across the entire front surface of the chestpiece 18. The circular support member 20 of the sheath is preferably constructed of a plastic material that is capable of retaining and maintaining its circular shape although constructing the circular support member 20 from a different material is within the scope of the present invention.

In addition, the sheath of the stethoscope shield device 10 of the present invention further includes a securing body 24 secured to the perimeter 22 of the circular support member 20 at the perimeter of the chestpiece 18 of the stethoscope 12. The securing body 24 has an aperture 26 for extending around the stethoscope 12 when the sheath is positioned thereon. Preferably, the securing body 24 is constructed of a durable, thin plastic material, a material thinner and more flexible than the material for the circular support member 20 although constructing the securing body 24 from a different material is within the scope of the present invention.

The stethoscope shield device 10 of the present invention further includes an elastic band 28 encircling the aperture 26 formed in the securing body 24. The elastic band 28 facilitates releasable securement of the sheath to the stethoscope 12 and maintains a snug, tight fit around the stethoscope 12.

Furthermore, the stethoscope shield device 10 of the present invention includes an attachment/removal mechanism 30 for assisting the user in attaching and removing the sheath without actually touching the sheath. In a preferred embodiment, the attachment/removal mechanism 30 is a pair of tabs 32 positioned around the aperture 26 adjacent the elastic band 28. The tabs 32 have one end mounted to the securing body 24 and the other end being free from attachment. The tabs 32 are preferably positioned across from each other on either side of the aperture 26 with the free end being maneuverable upward allowing a user to grasp the free ends of the tabs 32 to attach and/or remove the sheath from the stethoscope 12.

It should be noted, as discussed above, that the chestpieces 18 of stethoscopes 12 are available in different sizes. Therefore, the stethoscope shield device 10 of the present invention can be constructed in various sizes to cover one or both sides of the stethoscope chestpiece 18 and/or different sized stethoscope chestpieces 18.

Fairly simple in design yet extremely effective in application, the stethoscope shield device 10 of the present invention is placed around the metallic chestpiece 18 of the stethoscope 12. After the medical professional has performed the necessary task for the patient, the stethoscope shield device 10 is removed from the stethoscope 12 and disposed of in a proper biohazard receptacle (the same used for disposable gloves and similar items). For the next patient, the process is repeated. Used as intended, the stethoscope shield device 10 handily reduces the risk of transferring germs and bacteria between patients in the medical setting. Ideal for use by doctors, nurses, nurse's aides, EMTs, and other medical professionals, the stethoscope shield device 10 offers a protective means of shielding these professionals from possible lawsuits, resulting in lower malpractice insurance premiums. Another advantage for patients is that the stethoscope shield device 10 eliminates the cold, uncomfortable feeling that is common when the metal stethoscope chestpiece 18 is placed against the skin. Not just for human patients, the stethoscope shield device 10 proves invaluable to veterinarians, as the stethoscope shield device 10 can also help prevent the transfer of bacteria, fleas, and worms from pet to pet.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A stethoscope shield device for protecting a chestpiece of a stethoscope, the chestpiece having a diaphragm side and a bell side, the stethoscope shield device comprising:
   a support member for covering at least a portion of the diaphragm side of the chestpiece, the support member having a perimeter edge, the support member constructed for retaining and maintaining a desired shape;
   a securing body secured to the perimeter of the support member and covering at least a portion of the bell side of the chestpiece, the securing body having an aperture positionable about the chestpiece between the diaphragm side and the bell side; and
   a pair of tabs positioned around the aperture adjacent the elastic band, the tabs having one end mounted to the securing body and the other end being free from attachment, the free end being maneuverable in a generally upward direction sufficient for a person to grasp the free ends of the tabs;
   an elastic band encircling the aperture formed in the securing body;
   wherein the elastic band releasably secures the stethoscope shield device to the stethoscope and maintains a snug, tight fit around the chestpiece of the stethoscope.

2. The stethoscope shield device of claim 1 wherein the support member is circular.

3. The stethoscope shield device of claim 2 wherein the support member covers the entire side of the chestpiece, the perimeter edge of the support member substantially aligning with an edge of one of the sides of the chestpiece of the stethoscope.

4. The stethoscope shield device of claim 1 wherein the support member is constructed of a plastic material for inhibiting contamination of the chestpiece.

5. The stethoscope shield device of claim 1 wherein the securing body is constructed from a material different than the material of the support member.

6. The stethoscope shield device of claim 5 wherein the securing body material is thinner and more flexible than the support member material.

7. The stethoscope shield device of claim 1 wherein the pair of tabs includes a first tab and a second tab, the first tab being positioned substantially opposite the second tab.

8. A method for protecting a chestpiece of a stethoscope, the chestpiece having a diaphragm side and a bell side, the method comprising:
   providing a support member having a perimeter edge;
   covering at least a portion of the diaphragm side sides of the chestpiece with the support member, the support member having a perimeter edge;
   retaining and maintaining a desired shape of the support member;
   providing a securing body having an aperture;
   covering at least a portion of the bell side of the chestpiece;
   securing the securing body to the perimeter of the support member;
   positioning a pair of tabs around the aperture adjacent the elastic band;
   mounting one end of the tabs to the securing body;
   maintaining an other end of the tabs free;
   maneuvering the free end in a generally upward direction sufficient for a person to grasp the free ends of the tabs;
   positioning the aperture about the chestpiece between the diaphragm side and the bell side;
   encircling the aperture with an elastic band;
   releasably securing the stethoscope shield device to the stethoscope; and maintaining a snug, tight fit around the chestpiece of the stethoscope.

9. The method of claim 8 wherein the support member is circular.

10. The method of claim 9 and further comprising:
covering the entire side of the chestpiece with the support member; and
substantially aligning the perimeter edge of the support member with an edge of one of the sides of the chestpiece of the stethoscope.

11. The method of claim 8 and further comprising:
constructing the support member a plastic material for inhibiting contamination of the chestpiece.

12. The stethoscope shield device of claim 1 wherein the securing body is constructed from a material different than the material of the support member.

13. The method of claim 12 wherein the securing body material is thinner and more flexible than the support member material.

14. The method of claim 8 and further comprising:
assisting in attaching and removing the stethoscope shield device to the chestpiece of the stethoscope.

15. The method of claim 8 wherein the pair of tabs includes a first tab and a second tab, and further comprising:
positioning the first tab being substantially opposite the second tab.

16. A stethoscope shield device for protecting a chestpiece of a stethoscope, the chestpiece having a diaphragm side and a bell side, the stethoscope shield device comprising:
a support member for covering at least a portion of the diaphragm side of the chestpiece, the support member having a perimeter edge, the support member constructed for retaining and maintaining a desired shape;
a securing body secured to the perimeter of the support member and covering at least a portion of the bell side of the chestpiece, the securing body having an aperture positionable about the chestpiece between the diaphragm side and the bell side;
an elastic band encircling the aperture formed in the securing body; and
a pair of tabs positioned around the aperture adjacent the elastic band, the tabs having one end mounted to the securing body and the other end being free from attachment, the free end being maneuverable in a generally upward direction sufficient for a person to grasp the free ends of the tabs;
wherein the elastic band releasably secures the stethoscope shield device to the stethoscope and maintains a snug, tight fit around the chestpiece of the stethoscope; and
wherein the securing body material is thinner and more flexible than the support member material.

17. The stethoscope shield device of claim 16 wherein the support member is circular, the support member covering the entire side of the chestpiece, the perimeter edge of the support member substantially aligning with an edge of one of the sides of the chestpiece of the stethoscope.

18. The stethoscope shield device of claim 16 wherein the securing body is constructed from a material different than the material of the support member.

19. The stethoscope shield device of claim 16 wherein the pair of tabs includes a first tab and a second tab, the first tab being positioned substantially opposite the second tab.

* * * * *